United States Patent [19]
Fischetti et al.

[11] Patent Number: 5,968,763
[45] Date of Patent: Oct. 19, 1999

[54] METHOD FOR SCREENING INHIBITORS OF THE ENZYME WHICH CLEAVES THE ANCHOR OF SURFACE PROTEINS FROM GRAM POSITIVE BACTERIA

[75] Inventors: Vincent A. Fischetti, West Hempstead; Vijaykumar Pancholi, New York, both of N.Y.

[73] Assignee: The Rockefeller University, New York, N.Y.

[21] Appl. No.: 08/819,444

[22] Filed: Mar. 17, 1997

Related U.S. Application Data

[63] Continuation-in-part of application No. 08/319,540, Oct. 7, 1994.

[51] Int. Cl.$^6$ .............................. C12Q 1/37; C12N 9/50; C12N 9/52; C12N 9/54
[52] U.S. Cl. ........................... 435/23; 435/219; 435/220; 435/221
[58] Field of Search .................................... 435/219, 220, 435/221, 23

[56] References Cited

U.S. PATENT DOCUMENTS

| | | | |
|---|---|---|---|
| 4,598,044 | 7/1986 | Kricka et al. | 435/29 |
| 5,235,039 | 8/1993 | Heath, Jr. et al. | 430/328 |

OTHER PUBLICATIONS

H.F. Jenkinson, "Anchorage and Release of Gram–Positive Bacterial Cell–Surface Polypeptides", *Trends Microbiol.,* vol. 3, No. 9, Sep. 1995, pp. 333–335.

V.A. Fischetti et al., "Conservation of a Hexapeptide Sequence in the Anchor Region of Surface Proteins form Gram–Positive Cocci", *Molec. Microbiol.,* vol. 4, No. 9, 1990, pp. 1603–1605.

V. Pancholi et al., "Identification of an Endogenous Membrane Anchor–cleaving Enzyme for Group A Streptococcal M Protein", *J. Exp. Med.,* vol. 170, No. 6, Dec. 1989, pp. 2119–2133.

W.W. Navarre et al., "Proteolytic Cleavage and Cell Wall Anchoring at the LPXTG Motif of Surface Proteins in Gram–Positive Bacteria", *Molec. Microbiol.,* vol. 14, No. 1, Oct. 1994, pp. 115–121.

O. Schneewind et al., "Cell Wall Sorting Signals in Surface Proteins of Gram–Positive Bacteria", *Embo J.,* vol. 12, No. 12, Dec. 1993, pp. 4603–4611.

S. Dramsi et al., "Common Features of Gram–Positive Bacterial Proteins Involved in Cell Recognition", *Molec. Microbiol.,* vol. 9, No. 5, Sep. 1993, pp. 1119–1122.

S.F. Lee, "Identification and Characterization of a Surface Protein–Releasing Activity in Streptococcus Mutans and Other Pathogenic Streptococci", *Infect. Immun.,* vol. 60, No. 10, Oct. 1992, pp. 4032–4039.

O. Schneewind et al., "sorting of Protein A to the Staphylococcal Cell Wall", *Cell,* vol. 70, Jul. 1992, pp. 267–281.

O. Schneewind et al., "Structure of the Cell Wall Anchor of Surface Proteins in Staphylococcus Aureus", *Science,* vol. 268, No. 5207, Apr. 1995, pp. 103–106.

Vijaykumar Pancholi and Vincent A. Fischetti, "Identification of an Endogenous Membrane Anchor–Cleaving Enzyme for Group A Streptococcal M Protein", *J. Exp. Med.* The Rockefeller University Press (1989) 170:2119–2133.

Vijaykumar Pancholi and Vincent A. Fischetti, "Isolation and Characterization of the Cell–Associated Region of Group A Streptococcal M6 Protein", *Journal of Bacteriology* (1988) pp. 2618–2624.

Olaf Schneewind, Peter Model, and Vincent A. Fischetti, "Sorting of Protein A to the Staphylococcal Cell Wall", *Cell* (1992) 70:267–281.

*Primary Examiner*—Jon P. Weber

[57] ABSTRACT

The invention relates to an enzyme which cleaves surface proteins of gram-positive bacteria, to methods of detecting the enzyme, and methods of isolating the enzyme. In particular, the enzyme is isolated from a group A Streptococcus, and cleaves at the sequence LPXTGX (SEQ ID NO:1). A method for screening putative inhibitors of the enzyme which cleaves the anchor region of surface proteins from gram positive bacteria is also disclosed.

21 Claims, 4 Drawing Sheets

METHOD FOR SCREENING INHIBITORS OF THE ENZYME WHICH CLEAVES THE ANCHOR OF SURFACE PROTEINS FROM GRAM POSITIVE BACTERIA

RELATED APPLICATIONS

This application is a continuation-in-part of U.S. application Ser. No. 08/319,540, filed Oct. 7, 1994.

BACKGROUND OF THE INVENTION

1. Field of the Invention

The present invention relates to an enzyme for cleaving within the wall anchor region of a surface protein of a gram-positive bacterium, methods for detecting that enzyme in vivo and in vitro, and methods for purifying that enzyme. In particular, the enzyme is isolated from a group A Streptococcus, and cleaves the anchor region of streptococcal M protein.

2. Description of the Related Art

Bacteria may be designated as gram-positive and gram-negative, based on the staining of their cell walls with Gram's stain. Within the broad division of gram-positive bacteria are the gram-positive cocci, which include the genera Aerococcus, Corprococcus, Deinobacter, Deinococcus, Enterococcus, Gemella, Lactococcus, Leuconostoc, Marinococcus, Melissococcus, Micrococcus, Pediococcus, Peptococcus, Peptostreptococcus, Planococcus, Ruminococcus, Saccharococcus, Salinicoccus, Carcina, Staphylococcus, Stomatococcus, Streptococcus, Trichococcus, Vagococcus, Listeria and Actinomyces. In gram-positive bacteria, proteins are secreted into the surrounding medium, whereas in gram-negative bacteria, secretion occurs into the periplasmic space between the cytoplasmic and outer membranes (Model and Russel (1990) Cell 61:739–741; Schatz and Beckwith (1990) Ann. Rev. Genet. 24:215–248). Prokaryotic sorting signals are conceivable for the local assembly of supramolecular structures like pili (Strom and Lory, (1987) J. Bacteriol. 169:3181–3188), flagella (Loewy et al (1987) Genes Dev. 1:626–635), and bacteriophages (Brissette and Russel (1990) J. Mol. Biol. 211:565–580), or for localization of proteins in defined bacterial compartments. Such compartments include the outer membrane of gram-negative bacteria (Model and Russel (1990) Cell 61:739–741), the cell wall (Braun et al (1970) Eur. J. Biochem. 13:336–346; Eur. J. Biochem. 14:387–391; Biochemistry 9:5041–5049; Shockman and Barrett (1983) Annu. Rev. Microbiol. 37:501–527), and the periseptal annulus (MacAlister et al (1983) Proc. Natl. Acad. Sci. 80:1372–1376).

The cell wall of gram-positive bacteria can be thought of as representing a unique cell compartment, which contains anchored surface proteins that require specific sorting signals. Some biologically important products are anchored in this way, including protein A and fibronectin binding proteins of Staphylococcus aureus and M protein from Streptococcus pyogenes. Studies of staphylococcal Protein A and E. coli alkaline phosphatase show that the signal both necessary and sufficient for cell wall anchoring consists of an LPXTGX motif (SEQ ID NO:1), a C-terminal hydrophobic domain, and a charged tail. These sequence elements are conserved in many surface proteins from different gram-positive bacteria.

M protein of group A streptococci, an α-helical coiled-coil fibrillar molecule found on the surface of the organism (Fischetti et al (1988) Proteins Struct. Func. Genet. 3:60), is responsible for the antiphagocytic property of these bacteria (Lancefield et al (1962) J. Immunol. 89:307). Antigenic variation (Jones et al (1988), Proc. Natl. Acad. Sci. USA 85:8271) and type-specific immunity are contingent upon epitopes located within the NH$_2$-terminal half of the M molecule (distal to the cell wall) (Jones et al (1988) J. Exp. Med. 167:1114). Amino acid sequences that are conserved among different M proteins are located in the COOH-terminal half (Jones et al (1985) J. Exp. Med. 161:623; Hollingshead et al (1987) Infect. Immun. 55:3237) and contain epitopes recently shown to be responsible for non-type-specific immunity against streptococcal colonization (Bessen et al (1988) Infect. Immun. 56:2666; Fischetti et al (1989) Science 244:1487).

The attachment region of the molecule, predicted from DNA sequence, is located at the COOH terminal end, composed of charged amino acids at the COOH terminus, followed by 19 hydrophobic amino acids suspected to be a membrane anchor followed by a hexapeptide motif, LPXTGX. This region is adjacent to a proline and glycine-rich region situated within the peptidoglycan layer of the cell wall (Fischetti (1988) Proteins Struct. Func. Genet. 3:60; Pancholi et al (1988) J. Bacteriol. 170:2618; Hollingshead et al (1986), J. Biol. Chem. 261:1677.)

The association of the M protein to the cytoplasmic membrane of gram-positive bacteria can be examined after removing the cell wall with the muralytic enzyme lysin (Fischetti et al. (1974) Streptococcal Disease and the Community, M. J. Haverkorn, editor. Excerpta Medica, Amsterdam. 26.), which is active against group A streptococcal cell walls over a broad pH range. M protein is released during the removal of the cell wall indicating that an endogenous factor mediates this release (Pancholi et al (1989) J. Exp. Med. 170:2119–2133).

Analysis of the released form of the M protein demonstrates that the COOH-terminal 19 hydrophobic amino acids and charged tail of the M molecule are not present (Pancholi et al (1989) J. Exp. Med. 170:2119–2133). This suggests that the release of M proteins from the membrane and its attachment to the cell wall is in some way associated with the cleavage of the COOH-terminal hydrophobic region.

Cleavage of the surface proteins of gram-positive bacteria in the LPXTGX region adjacent to the hydrophobic domain has been shown to occur during the anchoring process of these proteins (Schneewind et al (1992) Cell 70:267–281). Because interference with this cleavage prevents the proper placement of surface proteins on the bacterial cell, characterization of the enzyme responsible for this cleavage would be a critical step in antibiotic development.

Therefore, it is apparent that what is needed in this art is a method of detecting and isolating this gram-positive bacterial surface protein cleavage enzyme.

SUMMARY OF THE INVENTION

Accordingly, a major object of the present invention is to provide an isolated and purified enzyme which cleaves surface proteins of gram-positive bacteria within the LPXTGX motif.

Another object of the present invention is to provide an antibody directed to the cleaving enzyme of gram-positive bacteria.

Yet another object of the present invention is to provide a method of detecting the presence of the cleaving enzyme of gram-positive bacteria within the LPXTGX motif.

A still further object of the present invention is to provide a method of isolating an enzyme which cleaves surface proteins on gram-positive bacteria.

Briefly, the present invention features an enzyme which cleaves a surface protein on gram-positive bacteria, and methods of detecting it. Detection methods of the present invention comprise the steps of:

(a) providing a peptide comprising an amino acid sequence of LPXTGX (SEQ ID NO:1), wherein said peptide is labeled with a detectable marker and covalently linked to a solid support;
(b) mixing the labeled, linked peptide with a membrane extract of grampositive bacteria;
(c) detecting a release of label from the support; and
(d) correlating the release of label with the presence of the enzyme. This method may be easily adapted to screen for inhibitors of the enzyme, by adding the suspected inhibitor to the mixture of step (b) above, and assessing the change in release of label compared to a control preparation (i.e., assay run in the absence of the putative inhibitor).

The present invention also provides a method for assessing the activity of the enzyme of the present invention in intact microorganisms, and screening for inhibitors of the enzyme, comprising the steps of:

(a) preparing a culture of the microorganisms in a suitable culture medium;
(b) growing said microorganisms in culture for a suitable period of time;
(c) separating the microorganisms from the culture media;
(d) detecting the presence of released surface proteins in the culture media; and
(e) comparing the amount of released surface proteins in the medium with inhibitor to the amount of released surface proteins in a control medium without inhibitor in order to determine the inhibition of enzyme activity.

The invention also features antibodies directed to that cleaving enzyme, and inhibitors of that enzyme.

The invention also features a method of isolating the cleaving enzyme, including the steps of:

(a) preparing a membrane extract of the gram-positive bacteria containing membrane-bound proteins;
(b) fractionating the membrane-bound proteins by chromatography using a salt gradient; and
(c) identifying the presence of the enzyme in at least one fraction.

With the foregoing and other objects, advantages and features of the invention that will become hereinafter apparent, the nature of the invention may be more clearly understood by reference to the following detailed description of the preferred embodiments of the invention and to the appended claims.

DETAILED DESCRIPTION OF THE PREFERRED EMBODIMENTS OF THE INVENTION

Figure 1:
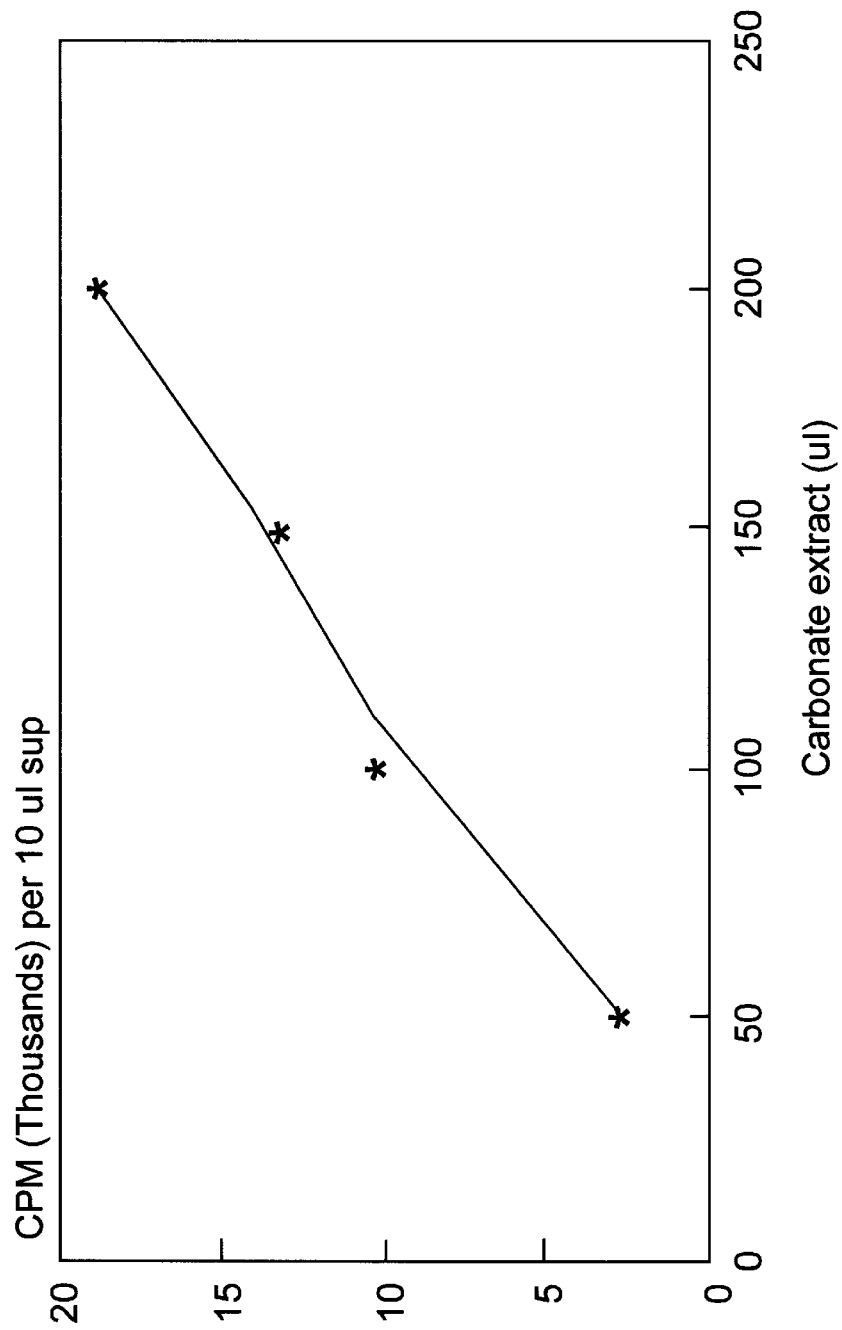
FIG. 1 is a dose-response curve with the dialyzed carbonate extract of D471 membranes.

More particularly, the present invention relates to methods for detecting and purifying a cleavage enzyme which cleaves surface proteins of gram-positive bacteria at a known motif, preferably an LPXTGX (SEQ ID NO:1) motif, and also relates to the purified cleavage enzyme itself.

The cleavage enzyme can be isolated from any gram-positive bacterium. Such gram-positive bacteria include the genera Aerococcus, Corprococcus, Deinobacter, Deinococcus, Enterococcus, Gemella, Lactococcus, Leuconostoc, Marinococcus, Melissococcus, Micrococcus, Pediococcus, Peptococcus, Peptostreptococcus, Planococcus, Ruminococcus, Saccharococcus, Salinicoccus, Carcina, Staphylococcus, Stomatococcus, Streptococcus, Trichococcus, Vagococcus, Listeria and Actinomyces. Gram-positive bacteria known to have surface proteins containing an LPXTGX (SEQ ID NO:1) motif include the following:

| SPECIES | PROTEIN | MOTIF | |
|---|---|---|---|
| A. naeslundii | fimbriae type 1 | LPLTGA | (SEQ ID NO:2) |
| A. viscosis | fimbriae type 1 | LPLTGA | (SEQ ID NO:2) |
| E. faecalis | Asa1 | LPQTGE | (SEQ ID NO:3) |
| E. faecalis | Asc10 | LPKTGE | (SEQ ID NO:4) |
| E. faecalis | Sec10 | LPQTGE | (SEQ ID NO:5) |
| Group G strep | Protein G | LPTTGE | (SEQ ID NO:6) |
| L. monocytogenes | InlA | LPTTGD | (SEQ ID NO:7) |
| P. magnus | Protein L | LPKAGS | (SEQ ID NO:8) |
| S. aureus | Protein A | LPETGE | (SEQ ID NO:9) |
| S. aureus | FnBP-A | LPETGG | (SEQ ID NO:10) |
| S. aureus | FnBP-B | LPETGG | (SEQ ID NO:10) |
| S. aureus | Cna | LPKTGM | (SEQ ID NO:11) |
| S. agalactiae | Bac | LPYTGV | (SEQ ID NO:12) |
| S. cremoris | Wg2 | LPKTGE | (SEQ ID NO:4) |
| S. mutans | Pac | LPNTGE | (SBQ ID NO:13) |
| S. mutans | SpaP | LPNTGE | (SEQ ID NO:13) |
| S. mutans | WapA | LPSTGE | (SEQ ID NO:14) |
| S. pyogenes | Arp2 | LPSTGE | (SEQ ID NO:14) |
| S. pyogenes | Arp4 | LPSTGE | (SEQ ID NO:14) |
| S. pyogenes | FcRA | LPSTGE | (SEQ ID NO:14) |
| S. pyogenes | M2 | LPSTGE | (SEQ ID NO:14) |
| S. pyogenes | M5 | LPSTGE | (SEQ ID NO:14) |
| S. pyogenes | M6 | LPSTGE | (SEQ ID NO:14) |
| S. pyogenes | M12 | LPSTGE | (SEQ ID NO:14) |
| S. pyogenes | M24 | LPSTGE | (SEQ ID NO:14) |
| S. pyogenes | M49 | LPSTGE | (SEQ ID NO:14) |
| S. pyogenes | M57 | LPSTGE | (SEQ ID NO:14) |
| S. pyogenes | Protein H | LPSTGE | (SEQ ID NO:14) |
| S. pyogenes | SCP | LPTTND | (SEQ ID NO:15) |
| S. pyogenes | T6 | LPSTGS | (SEQ ID NO:16) |
| S. sobrinus | SpaA | LPATGD | (SEQ ID NO:17) |

A more preferred species for the present invention is *Streptococcus pyogenes*, and most preferred is M type 6.

The present invention also provides methods for detecting the enzyme of the present invention. Detection methods of the present invention comprise the steps of:

(a) providing a peptide comprising an amino acid sequence of LPXTGX (SEQ ID NO:1), wherein said peptide is labeled with a detectable marker and covalently linked to a solid support;
(b) mixing the labeled, linked peptide with a membrane extract of grampositive bacteria;
(c) detecting a release of label from the support; and
(d) correlating the release of label with the presence of the enzyme.

This method may be easily adapted to screen for inhibitors of the enzyme, by adding the suspected inhibitor to the mixture of step (b) above, and assessing the change in release of label compared to a control mixture (i.e., assay run in the absence of the putative inhibitor). The control mixture is preferably run contemporaneous with the mixture containing the inhibitor. Alternatively, the results from the mixture containing inhibitor may be compared to results obtained from a previous control mixture, or by other means.

Protoplasts may be prepared from the bacteria by any means known in the art. The culture is grown in any medium known to support the growth of the particular species, preferably Todd-Hewitt broth. Bacteria are preferably grown in culture for approximately 12 to approximately 24 hours, most preferably for approximately 18 hours. The cells are then centrifuged and washed. The cells are then resuspended in a phosphate buffer, preferably from about 20 to about 100 mM, more preferably about 50 mM, and preferably containing raffinose at about 10–50%, preferably about 30%, or sucrose at about 10–30%, preferably about 20%, and EDTA. An enzyme specific for degrading the cell wall, preferably a Group C streptococcal phage-associated lysin, is then added and incubated at approximately 37° C. for at least 30 minutes.

Membranes can be prepared from the protoplasts using any method known in the art, but preferably by suspension in hypotonic buffer and repeated freeze-thaw treatments in the presence of protease inhibitors and DNAase. Membranes are then collected by centrifugation at about 100,000×g, washed, and then resedimented in the presence of protease inhibitors.

As a method of analyzing cleavage activity of the enzyme, and especially for analyzing activity of cleavage enzyme mutants, target surface molecules can be prepared by releasing the surface molecules from the membrane using any method known in the art. Preferably, the surface molecule can be released by treating the membranes with sodium carbonate at a pH>9, preferably >11, most preferably at about 11.5.

The presence of surface protein, particularly M protein, in the separated growth medium can be identified using any method known in the art, including separation on SDS-PAGE gel, Western blot, enzyme-linked immunosorbent assay (ELISA), capture ELISA, RIA and the like. Antibodies for the detection of M protein are available in the art and include polyclonal sera, such as that against ColiM6.1 protein (Fischetti et al (1984) *J. Exp. Med.* 159:1083); polyclonal sera to a synthetic peptide corresponding to residues of the M protein, such as residues 1–21 (Jones et al (1988) *Proc. Natl. Acad. Sci. USA* 85:8271), or anti-SM6 (308–327) to residues 308–327, anti-SM6(339–352) to residues 339–352, or anti-SM6(381–398) to residues 381–398; or the monoclonal antibody 10B6 to an epitope in the conserved region of the M molecule between residues 275 and 289.

In general, monoclonals are used at a dilution of 1:100–1:10,000, preferably about 1:1000, and polyclonal sera are used at a dilution of about 1:50–1:5000, preferably about 1:500.

The cleavage enzyme is preferably detected by preparing a detectably labeled synthetic substrate. The labeled synthetic substrate preferably contains an LPXTGX (SEQ ID NO:1) sequence, and more preferably contains a LPSTGE (SEQ ID NO:14) sequence. Methods for the preparation and analysis of such a synthetic peptide are well known in the art.

The synthetic peptide can be labeled with any detectable label known in the art. Preferably, this label is an isotope, most preferably $^{125}$I. The labeled synthetic peptide is then preferably linked to a substrate which is preferably a solid support, more preferably a commercially available bead. Chromatographic beads for use in the present invention are preferably from about 10 to about 100 μm in diameter, more preferably about 50 to about 80 μm in diameter.

The bacterial strain containing the cleavage enzyme is treated to extract the bacterial membrane. Preferably, the bacterial membranes are treated with an alkaline buffer, preferably carbonate buffer, at a pH of about 9–13, preferably about 11.5. The extraction is preferably conducted at a temperature below room temperature, preferably at about 0° C. The membrane extract is then mixed with the labeled peptides in a suitable buffer, and release of radiolabel from the cleaved synthetic peptide is analyzed. In order to screen putative inhibitors of the enzyme, the putative inhibitor is added to the mixture of membrane extract (or isolated enzyme) and labeled peptides, and the release of radiolabel is compared to control preparations (run in the absence of the putative inhibitor).

The enzyme is isolated from the extract using protein purification methods well known in the art. In particular, the membrane extract containing the detected cleavage activity is subjected to chromatographic techniques which separate proteins present in the extract according to size, affinity and charge. Fractions obtained from each chromatographic step are analyzed for cleavage activity as described above, and subjected to further purification steps. A particularly preferable method for obtaining purified cleavage enzyme is high performance liquid chromatography (HPLC).

After the enzyme has been purified, its amino acid sequence can be determined using amino acid sequencing methods well known in the art. A particularly preferable method is Edman degradation. Having obtained sequence information on the cleavage enzyme, one can design oligonucleotide probes for isolating the DNA encoding the cleavage enzyme, using conventional screening methods, or amplification methods such as polymerase chain reaction (PCR). It is particularly preferable to design such oligonucleotides in a completely degenerate manner, such that oligonucleotides containing each codon encoding a particular amino acid are present in the oligonucleotide mix. Alternatively, inosine can be used at positions in the codon where degeneracies are known to be present.

In general, the procedures for isolating the DNA encoding the cleavage enzyme, subjecting it to partial digestion, isolating DNA fragments, ligating the fragments into a cloning vector, and transforming a host are well known in recombinant DNA technology. Accordingly, one of ordinary skill in the art can use or adapt the detailed protocols for such procedures as found in Sambrook et al. (1989), *Molecular Cloning: A Laboratory Manual*, 2nd. Ed., Cold Spring Harbor Laboratory, Cold Spring Harbor, N.Y., 3 volumes, or in any other manual on recombinant DNA technology.

Once the gene encoding the LPXTGX (SEQ ID NO:1) cleavage enzyme has been obtained from one species, it can serve as a hybridization probe to isolate corresponding genes from the other species by cross-hybridization under low to moderate stringency conditions. Such conditions are usually found empirically by determining the conditions wherein the probe specifically cross-hybridizes to its counterpart gene with a minimum of background hybridization. Nucleic acid hybridization is a well known technique and thoroughly detailed in Sambrook et al.

As noted above, the DNA encoding the cleavage enzyme can be originally isolated using PCR. Corresponding DNAs from other species can also be isolated using PCR, and oligonucleotides for performing these subsequent PCR reactions can be optimized using the sequence information obtained from DNA cloned from the first species.

A further aspect of the present invention provides the nucleic acids encoding the subject genes in replicable expression vectors and transformed hosts containing these vectors. The replicable expression vectors may also be used to obtain the polypeptides of the present invention by well known methods in recombinant DNA technology.

The instant replicable expression vectors comprise a nucleic acid encoding the subject gene, i.e., the coding sequence is operably linked in proper reading frame to a nucleotide sequence element which directs expression of the cleavage enzyme. In particular, the nucleotide sequence elements may include a promoter, a transcription enhancer element, a termination signal, a translation signal, or a combination of two or more of these elements, generally including at least a promoter element.

Replicable expression vectors are generally DNA molecules engineered for controlled expression of a desired gene, especially where it is desirable to produce large quantities of a particular gene product, or polypeptide. The vectors comprise one or more nucleotide sequences operably linked to a gene to control expression of that gene, the gene being expressed, and an origin of replication which is operable in the contemplated host. Preferably the vector encodes a selectable marker, for example, antibiotic resistance. Replicable expression vectors can be plasmids, bacteriophages, cosmids and viruses. Any expression vector comprising RNA is also contemplated. The replicable expression vectors of this invention can express the cleavage enzyme at high levels. Many of these vectors are based on pBR322, M13 and lambda and are well known in the art and employ such promoters as trp, lac, $P_L$, T7 polymerase and the like. Hence, one skilled in the art has available many choices of replicable expression vectors, compatible hosts, and well-known methods for making and using the vectors.

Moreover, peptides and fragments as well as chemically modified derivatives of the LPXTGX (SEQ ID NO:1) cleavage enzyme are also contemplated by the present invention. Briefly, any peptide fragment, derivative or analog which retains substantially the same biological activity of the LPXTGX (SEQ ID NO:1) cleavage enzyme is contemplated. An analog may be defined herein as a peptide or fragment which exhibits LPXTGX (SEQ ID NO:1) cleaving activity, but has an amino acid substitution, insertion or deletion in comparison to the wild-type cleavage enzyme. Such an analog can be prepared by the "conservative" substitution of an amino acid having similar chemical properties.

Thus, it should also be appreciated that also within the scope of the present invention are DNA sequences encoding an LPXTGX (SEQ ID NO:1) cleavage enzyme having the same amino acid sequence as the wild-type enzyme, but also those DNA sequences which are degenerate to the wild-type sequence. By "degenerate to" is meant that a different three-letter codon is used to specify a particular amino acid. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Termination codon | UAA (ochre) or UAG (amber) or UGA (opal) |

It should be understood that the codons specified above are for RNA sequences. The corresponding codons for DNA have T substituted for U.

Mutations can be made in the wild-type sequence such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The following is one example of various groupings of amino acids:

| Amino acids with nonpolar R groups | | | |
|---|---|---|---|
| Alanine | Valine | Leucine | Isoleucine |
| Proline | Phenylalanine | Tryptophan | Methionine |

| Amino acids with uncharged polar R groups | | | |
|---|---|---|---|
| Glycine | Serine | Threonine | Cysteine |
| Tyrosine | Asparagine | Glutamine | |

Amino acids with charged polar R groups (negatively charged at Ph 6.0)

| | | |
|---|---|---|
| Aspartic acid | Glutamic acid | |

Basic amino acids (positively charged at pH 6.0)

| | | |
|---|---|---|
| Lysine | Arginine | Histidine (at pH 6.0) |

Another grouping may be those amino acids with phenyl groups:

| | | |
|---|---|---|
| Phenylalanine | Tryptophan | Tyrosine |

Another grouping may be according to molecular weight (i.e., size of R groups):

| | | | |
|---|---|---|---|
| Glycine | 75 | Glutamine | 146 |
| Alanine | 89 | Lysine | 146 |
| Serine | 105 | Glutamic acid | 147 |
| Proline | 115 | Methionine | 149 |
| Valine | 117 | Histidine (at pH 6.0) | 155 |
| Threonine | 119 | Phenylalanine | 165 |
| Cysteine | 121 | Arginine | 174 |
| Leucine | 131 | Tyrosine | 181 |
| Isoleucine | 131 | Tryptophan | 204 |
| Asparagine | 132 | | |
| Aspartic acid | 133 | | |

Particularly preferred substitutions are:

Lys for Arg and vice versa such that a positive charge may be maintained;

Glu for Asp and vice versa such that a negative charge may be maintained;

Ser for Thr such that a free -OH can be maintained; and

Gln for Asn such that a free NH$_2$ can be maintained.

Amino acid substitutions may also be introduced to substitute an amino acid with a particularly preferable property. For example, a Cys may be introduced at a potential site for disulfide bridging with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

Purification of the subject LPXTGX (SEQ ID NO:1) cleavage enzyme from natural or recombinant sources can be accomplished by conventional purification means such as ammonium sulfate precipitation, gel filtration chromatography, ion exchange chromatography, adsorption chromatography, affinity chromatography, HPLC, FPLC, and the like. Where appropriate purification steps can be done in batch or in columns.

Peptide fragments of the LPXTGX (SEQ ID NO:1) cleavage enzyme can be prepared by proteolysis or by chemical degradation. Typical proteolytic enzymes are trypsin, chymotrypsin, V8 protease, subtilisin and the like; the enzymes are commercially available, and protocols for performing proteolytic digests are well known. Peptide fragments are purified by conventional means, as described above. Peptide fragments can often be identified by amino acid composition or sequence. Peptide fragments are useful as immunogens to obtain antibodies against the subject LPXTGX (SEQ ID NO:1) cleavage enzyme.

The present invention also relates to antibodies to the LPXTGX (SEQ ID NO:1) cleavage enzyme. Such antibodies may be monoclonal or polyclonal and are contemplated as being useful in developing detection assays (immunoassays) for cleavage enzyme proteins, monitoring cleavage enzyme levels and in purifying cleavage enzyme. Thus, in accordance with this invention, an antibody to an LPXTGX (SEQ ID NO:1) cleavage enzyme encompasses monoclonal or polyclonal antibodies to said LPXTGX (SEQ ID NO:1) cleavage enzyme, or to antigenic parts thereof.

Both polyclonal and monoclonal antibodies to the LPXTGX (SEQ ID NO:1) cleavage enzyme are obtainable by immunization of an animal with purified LPXTGX (SEQ ID NO:1) cleavage enzyme, purified recombinant LPXTGX (SEQ ID NO:1) cleavage enzyme, fragments of these proteins, or purified fusion proteins of LPXTGX (SEQ ID NO:1) cleavage enzyme with another protein. In the case of monoclonal antibodies, partially purified proteins or fragments may serve as immunogens. The methods of obtaining both types of antibodies are well known in the art with excellent protocols for antibody production being found in Harlow et al. (1988) *Antibodies: A Laboratory Manual*, Cold Spring Harbor Laboratory, Cold Spring Harbor, N.Y., 726 pp.

Polyclonal sera are relatively easily prepared by injection of a suitable laboratory animal with an effective amount of the purified LPXTGX (SEQ ID NO:1) cleavage enzyme, or parts thereof, collecting serum from the animal, and isolating specific sera by any of the known immunoadsorbent techniques. Antibodies produced by this method are useful in virtually any type of immunoassay.

Monoclonal antibodies are particularly useful because they can be produced in large quantities and with a high degree of homogeneity. Hybridoma cell lines which produce monoclonal antibodies are prepared by fusing an immortal cell line with lymphocytes sensitized against the immunogenic preparation and is done by techniques which are well known to those who are skilled in the art. (See, for example, Douillard, I. Y. and Hoffman, T., "Basic Facts About Hybridomas", in *Compendium of Immunology*, Vol. II, L. Schwartz (Ed.) (1981); Kohler, G. and Milstein, C., *Nature* 256: 495–497 (1975) and *European Journal of Immunology* 6: 511–519 (1976); Harlow et al.; Koprowski, et al., U.S. Pat. No. 4,172,124; Koprowski et al., U.S. Pat. No. 4,196,265 and Wands, U.S. Pat. No. 4,271,145, the teachings of which are herein incorporated by reference.

The presence of the LPXTGX (SEQ ID NO:1) cleavage enzyme in a sample, such as a culture supernatant and the like, in a microorganism, or in any other source suspected to contain the LPXTGX (SEQ ID NO:1) cleavage enzyme, can be detected utilizing antibodies prepared as above, either monoclonal or polyclonal, in virtually any type of immunoassay. Likewise, the present antibodies can be used to identify microorganisms which have or produce LPXTGX (SEQ ID NO:1) cleavage enzyme. Accordingly, the present invention provides a method of detecting an LPXTGX (SEQ ID NO:1) cleavage enzyme by the steps of contacting a sample suspected of containing said LPXTGX (SEQ ID NO:1) cleavage enzyme with an antibody of the invention for a time and under conditions sufficient to form an enzyme-antibody complex and subjecting this complex to a detecting means. As well known to one skilled in the art, the time and conditions for immunodetection assays are variable and depend on the particular assay.

A wide range of detection techniques and conditions are available to one skilled in the art as can be seen by reference to U.S. Pat. Nos. 4,016,043; 4,424,279 and 4,018,653 and to Harlow et al. which provides extensive protocols for immunodetection of molecules. These techniques, of course, include both single-site and two-site, or "sandwich" assays, assays of the noncompetitive types as well as competitive binding assays, ELISA, radioimmunoassays, immunoprecipitation and immunoblotting (Western blotting). Sandwich assays are commonly used, a number of variations of the technique exist, and all are intended to be encompassed by the present invention.

Direct and indirect immunoassays, i.e., ELISA, immunoblotting and the like, may employ reporter molecules linked to either a primary antibody (direct assay) or a second antibody or antibody-specific protein such as Protein A or Protein G (indirect assay). The primary antibody can be an antibody of the subject invention labelled with the desired reporter molecule.

By "reporter molecule," as used herein, is meant a molecule which, by its chemical nature, provides an identifiable signal to detect antigen-antibody complexes. Detection may be either qualitative or quantitative. The most commonly used reporter molecules are either enzymes, fluorophores, or radionuclide containing molecules (i.e., radioisotopes). In the case of an enzyme immunoassay, an enzyme is conjugated to the antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, β-galactosidase, and alkaline phosphatase among others. The substrate to be used with a particular enzyme is generally chosen for the production of a detectable color change upon reaction. For example, p-nitrophenyl phosphate is suitable for use with alkaline phosphatase conjugates; for peroxidase conjugates, 1,2-phenylenediamine, 5-aminosalicylic acid, or toluidine are commonly used. It is also possible to employ fluorogenic substrates, which yield a fluorescent product rather than the chromogenic substrates noted above. After binding an enzyme-labeled antibody to an antigen or antigen-antibody complex, as appropriate, the excess labeled antibody is washed away, and a solution containing the appropriate substrate is added. The substrate reacts with the enzyme, i.e., the reporter molecule, to give a qualitative visual signal or a quantitative signal which can be assessed to indicate the amount of antigen present in the sample.

Alternately, fluorescent compounds, such as fluorescein and rhodamine, may be chemically coupled to antibodies without altering their binding capacity. As used in immunofluorescence, when activated by illumination with light of a specific wavelength, a fluorophore-labeled antibody absorbs the light energy, inducing the fluorophore into an excited stated which is followed by emission of light having a characteristic wavelength. Generally, the emitted light is a characteristic color in the visible range and is detectable with a light microscope equipped for immunofluorescence. Fluorescent antibodies are used in sandwich assays, direct and indirect immunoassays as described above, except after washing, the immune complex is exposed to light of the appropriate wavelength, and the fluorescence is observed. Immunofluorescence and enzyme-based immunoassay techniques are both well established in the art and are particularly preferred. However, other reporter molecules, such as radioisotopes, chemiluminescent or bioluminescent molecules, may also be employed. It will be readily apparent to the skilled technician how to vary the procedure to suit the required purpose.

Another aspect of the invention provides a means of purifying an LPXTGX (SEQ ID NO:1) cleavage enzyme by affinity selection. This method involves contacting a sample containing the LPXTGX (SEQ ID NO:1) cleavage enzyme with an antibody of the invention, and separating the antigen-antibody complex, e.g., the enzyme-antibody complex from the remainder of the sample and recovering the enzyme in a form free from the antibody. Typically the complex-containing sample is fractionated and the fraction (s) containing the—enzyme are identified by a convenient biochemical, enzymatic, immunological or other detection means. To facilitate fractionation, the subject antibodies can be bound to a chromatography resin before or after binding to the cleavage enzyme. This method can yield purified cleavage enzyme in large amounts and in pure form.

Accordingly, the present invention is also directed to a kit for the rapid and convenient assay of an LPXTGX (SEQ ID NO:1) cleavage enzyme, in samples suspected of containing the enzyme. The kit may contain either an antibody directed to the LPXTGX (SEQ ID NO:1) cleavage enzyme, and a secondary detectable antibody thereto, or may contain a labelled substrate for the enzyme, such that a labelled cleavage product is detected in the presence of the cleavage enzyme.

Another aspect of the present invention is directed to a method of detecting the DNA or RNA encoding the subject LPXTGX (SEQ ID NO:1) cleavage enzyme by nucleic acid hybridization techniques such as Southern blotting, Northern blotting and the like, or by the polymerase chain reaction (PCR). Accordingly, a method of detecting a cleavage enzyme is provided which comprises contacting a sample suspected of containing said cleavage enzyme-encoding DNA with a first nucleic acid sufficiently complementary to hybridize to a second nucleic acid which encodes said cleavage enzyme in said sample for a time and under conditions sufficient to effect said hybridization and thereby form a complex of said first and second nucleic acids and subjecting said complex to a detecting means. In this method, the first nucleic acid may have a reporter group attached thereto. Reporter groups can include radioisotopes, enzymatically detected groups such as biotin or fluorophores such as rhodamine and fluorescein. Detailed methods for hybridization and blotting is found in Sambrook et al.

For PCR, the present method of detecting a gene encoding the LPXTGX (SEQ ID NO:1) cleavage enzyme comprises subjecting a sample suspected of containing the cleavage enzyme to a polymerase chain reaction (PCR) using at least two oligonucleotide primers sufficiently complementary to hybridize to a nucleic acid in said sample which encodes said cleavage enzyme, and thereby producing at least one amplified nucleic acid segment and identifying said segment. PCR has been described in U.S. Pat. Nos. 4,683,195; 4,683,202; and 4,800,159 which are incorporated herein by reference as well as described extensively in the literature, see for example Saiki et al. (1988), *Science* 239: 487–491. The segment may be detected by gel electrophoresis or blotting, for example.

Also encompassed by the present invention are inhibitors of the cleavage enzyme which can be routinely screened using the cleavage assay described above.

The present invention also provides a method for assessing the activity of the enzyme of the present invention in intact microorganisms, and screening for inhibitors of the enzyme, comprising the steps of:

(a) preparing a first culture of the microorganisms in a suitable culture medium further comprising the suspected inhibitor;

(b) growing said microorganisms in culture for a suitable period of time;

(c) separating the microorganisms from the culture media;

(d) detecting the presence of released surface proteins in the culture media; and (e) comparing the amount of released surface proteins in the medium with inhibitor to the amount of released surface proteins in a control medium (i.e., without inhibitor) in order to determine the inhibition of enzyme activity.

Preferably, the control culture is run contemporaneous with the culture containing the suspected inhibitor. Alternatively, the results from culture containing inhibitor may be compared to results obtained from a previous control culture, or derived by other means.

The microorganisms for use in the method of the present invention are preferably gram-positive bacteria, more preferably of the genus Streptococcus, still more preferably *S. pyogenes*. Culture media suitable for growing microorganisms according to the method of the present invention are known in the art and may easily be selected by one of ordinary skill to be suitable to the chosen microorganism without the need for undue experimentation. Culture media may contain labeled amino acids that are incorporated into surface proteins by the selected microorganisms. Labeled amino acids are known in the art and may be selected by one of ordinary skill to be suitable to the chosen microorganism and the surface protein of interest without the need for undue experimentation. Suitable labels that may be incorporated into amino acids are discussed in detail above. Microorganisms are preferably grown in culture for approximately 12 to approximately 24 hours, preferably for approximately 18 hours.

Methods of separating microorganisms from culture media are known in the art, and one of ordinary skill in the art can select a suitable method without the need for undue experimentation. A preferred method of separating the microorganisms from the culture medium is via centrifugation. Centrifugation parameters must be chosen carefully so as to leave the microorganisms intact.

Following the separation of microorganisms from the culture medium, the culture medium is then subjected to an assay suitable to detect the presence of released surface proteins. The presence of surface protein, particularly M protein, in the supernatant can be identified using any method known in the art, including separation on SDS-PAGE gel, Western blot, enzyme-linked immunosorbent assay (ELISA), capture ELISA, RIA, immunoprecipitation, and the like.

As noted above, antibodies for the detection of M protein are available in the art and include polyclonal sera, such as that against ColiM6.1 protein; polyclonal sera to a synthetic peptide corresponding to residues of the M protein, such as residues 1–21, or anti-SM6(308–327) to residues 308–327, anti-SM6(339–352) to residues 339–352, or anti-SM6 (381–398) to residues 381–398; or the monoclonal antibody 10B6 to an epitope in the conserved region of the M molecule between residues 275 and 289. Methods suitable for generating antibodies, to M protein or to other proteins, are discussed in detail above.

Alternatively, if labeled amino acids have been incorporated into the surface proteins, detection methods suitable to detect the selected label are known in the art and will easily be chosen by one of ordinary skill in the art. Suitable assays that may be used to detect labeled proteins in the present method are discussed in detail above.

The following examples are presented in order to more fully illustrate the preferred embodiments of the invention. They should in no way be construed, however, as limiting the broad scope of the invention.

EXAMPLE 1

Preparation of a Synthetic Substrate for the Detection of Cleavage Activity

A synthetic peptide was designed having the following amino acid sequence (SEQ ID NO:18):
KRQLPSTGETANPFY
This peptide was prepared by the solid-phase method of Barany and Merrifield (1979) In Gross and J. Meienhofer, (ed.), Academic Press, Inc., New York, p. 1–284, which is hereby incorporated by reference in its entirety, and purified by high pressure liquid chromatography on a Brownlee C8 reverse-phase column (Brownlee Laboratories, Santa Clara, Calif.) with a gradient of acetonitrile in 0. 05 % trifluoroacetic acid. The sequence was verified by amino acid composition and sequence analysis as follows:

For amino acid analysis, peptides were hydrolyzed in 6 N HCl at 110° C. for 22 hours and derivatized with ethanol-triethylamine-water-phenylisothiocyanate (7:1:1:1) in a Picotag Work Station (Waters Associates, Inc., Milford, Mass.) and analyzed with a Novapak C18 column (Waters) and a Waters 840 Data Module.

Amino acid sequence analysis was performed by automated Edman degradation in a model 470A gas phase sequencer (Applied Biosystems, Foster City, Calif.). The phenylhydantoin amino acids were identified by high-pressure liquid chromatography on a C18 column with either a 1084B analyzer (Hewlett-Packard Co, Rockville, Md.) or a model 120A PTH analyzer (Applied Biosystems). For amino sugar analysis, peptides were hydrolyzed in 4 N HCl at 100° C. for 7 hours. They were then derivatized and analyzed as described above for amino acid analysis with a Novapak C18 column (Waters).

The purified peptide contained the LPSTGE (SEQ ID NO:14) sequence flanked on either side by amino acids found in this position in the streptococcal M protein molecule. As a marker, the peptide was sequenced with a tyrosine (Y) at the C-terminal end so that it could be labeled with $^{125}$I.

The peptide was radiolabeled with $^{125}$I using Iodobeads and then the labeled peptide was purified on a Sephadex G10 column and covalently linked by its N-terminal end by EDC (ethyl-3-(3 diethylaminopropyl)carbodiimide HCl) to an extended arm on a commercially available bead (3M Emphase Biospheres AB1 from Pierce, Rockford, Ill.), and the excess radiolabel removed by washing the beads with 1 M NaCl buffer.

EXAMPLE 2

Detection of Cleavage Activity in Streptococcal Membrane Extracts

M type 6 streptococcal strain D471 was treated with 0.1 M sodium carbonate (pH 11.5) and incubated for 30 minutes at 0° C. to extract the streptococcal membranes.

Figure 2:
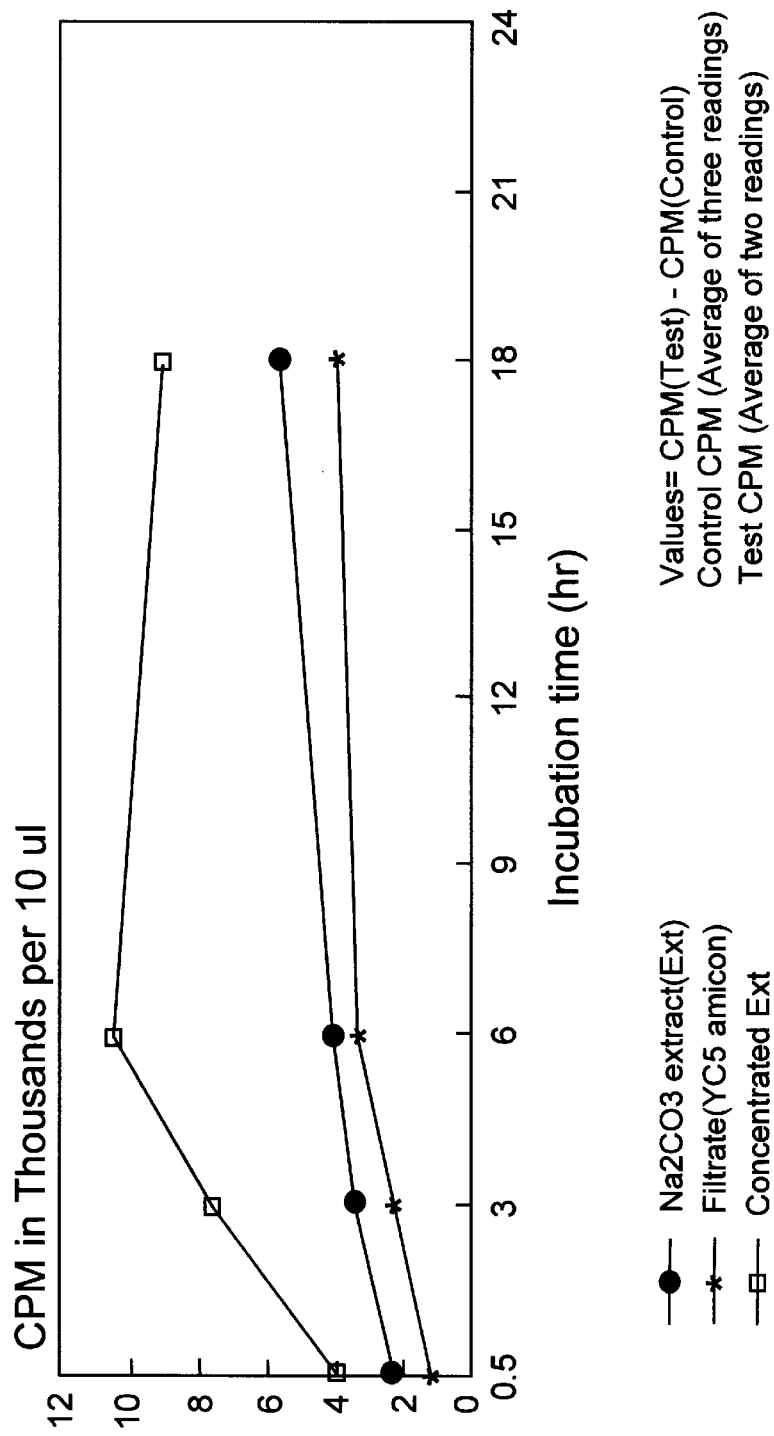
FIG. 2 is a time-response curve using a carbonate extract of D471 membranes.

The resulting extract was mixed with the labeled beads of Example 1 (50 μl sample, 50 μl 50 mM Tris HCl (pH 8.0) with 10 mM DTT). Radiolabel was released in a time- and dose-dependent manner, as seen in FIGS. 1 and 2. Controls using nonionic detergent, and buffers containing a high concentration of salt were unable to release the enzymatic activity suggesting that the cleaving enzyme activity was firmly associated with the streptococcal membrane. However, membranes extracted with 0.1 M sodium carbonate pH 11.5 demonstrated cleavage activity.

EXAMPLE 3

Isolation of the Cleaving Enzyme

The carbonate extract was chromatographed on a 20 HQ perfusion chromatography column, using a Biocad Sprint instrument (Perceptive Biosystem), employing a NaCl gradient from 0 mM to 500 mM (24.9 ml) followed by a 500 mM to 1000 mM (33.2 ml) gradient. To measure the enzyme activity found in the fractions, a 50 μl sample from each fraction was mixed in a reaction buffer in a final volume of 100 μl containing 5 mM DTT and 5 μl of the bead-substrate as described in Example 1. Control samples containing only buffer and the substrate were also mixed and incubated at 37° C. for 4 hours under constant slow rotation. The released radioactivity was then measured in 25 μl of the supernatant obtained after centrifugation. The specific activity was measured after subtracting the control values from the test samples.

The enzyme activity was eluted in one peak obtained between 0.6 M to 0.7 M NaCl (i.e., 37.5–43.2 mSiemans of conductivity) gradient in a total of 6 fractions of 1 ml each. The specific released radioactivity in these fractions was found to be between 6,000 to 11,000 cpm as compared to other fractions where the values varied form 0 to 1000 cpm.

EXAMPLE 4

Properties of the Cleavage Enzyme

Figure 3:
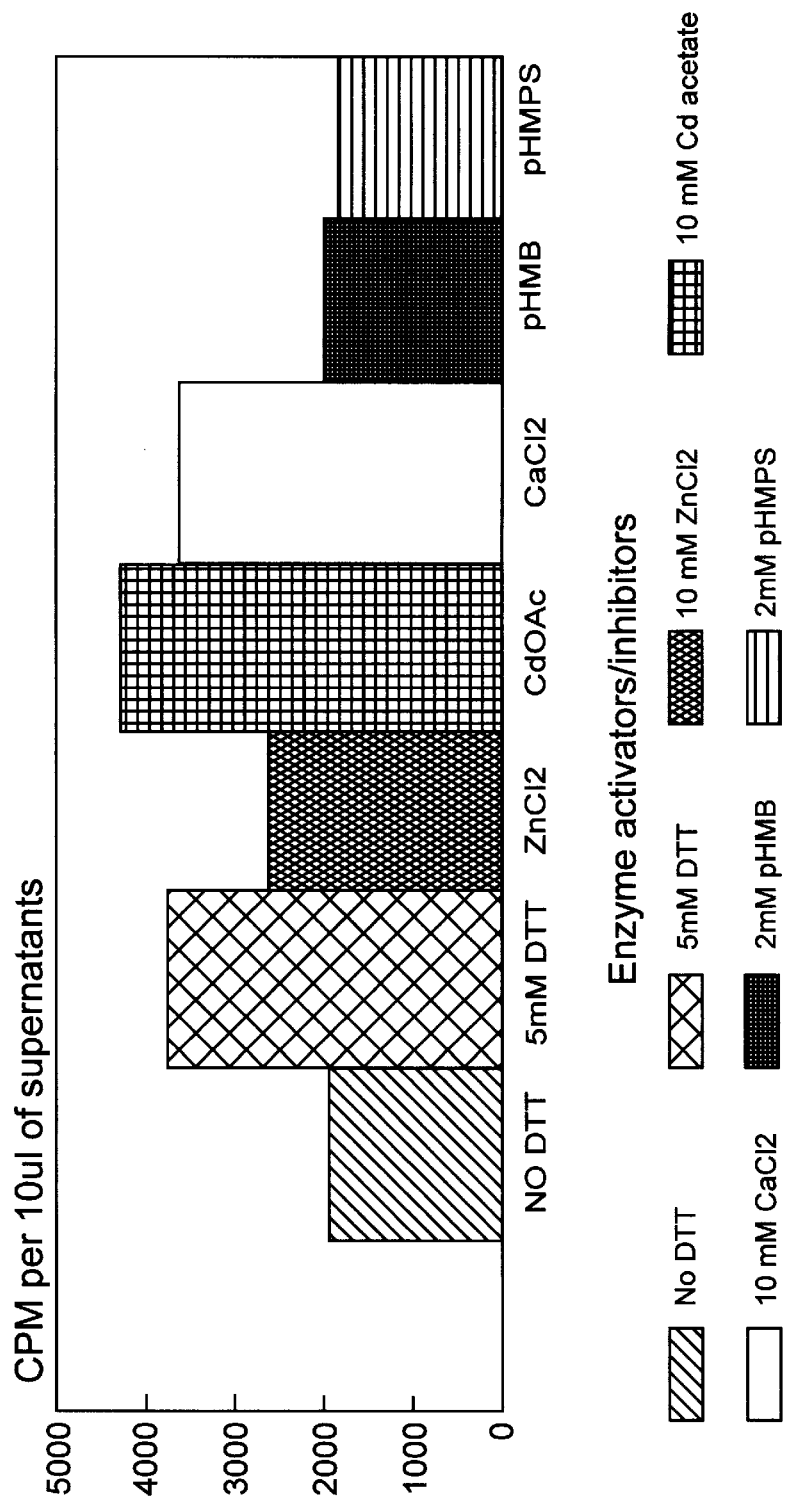
FIG. 3 shows the cleavage activity of the enzyme in the present of enzyme inhibitors and activators.
Figure 4:
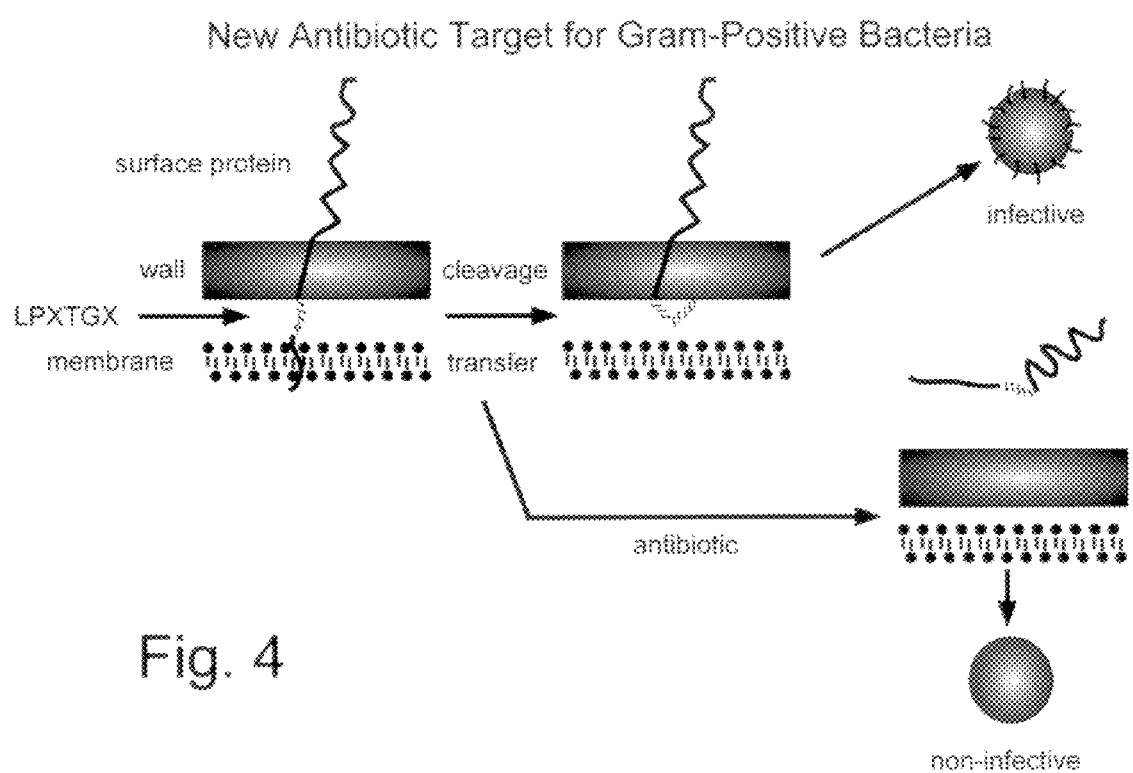
FIG. 4 is a schematic illustrating the positioning of the surface protein in the bacterial membrane, and the cleavage step which leads to infective bacteria. An antibiotic directed to the cleavage step results in non-infective bacteria.

FIG. 3 illustrates the enzymatic activity of the carbonate extract of the membranes (as the enzyme source) in the presence of various inhibitors and activators.

Activity was found to be enhanced in the presence of 5 mM DTT and divalent cations such as calcium.

1 mM each of parahydroxymercuribenzoic acid (PHMB) and parahydroxymercuriphenylsulfonic acid (PHMPS) inhibited cleavage activity.

These results indicate that the enzyme is sulfhydryl dependant.

EXAMPLE 5

Determination of the Site of Cleavage

Cleaved labeled synthetic peptide is analyzed using C-terminal sequencing and/or amino acid analysis to determine the exact site of cleavage, and optimal flanking regions to the target LPXTGX (SEQ ID NO:1) site.

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

What is claimed is:

1. A method for screening suspected inhibitors of an enzyme that cleaves surface proteins of gram-positive bacteria at the LPXTGX motif, comprising the steps of:
   (a) providing a peptide comprising an amino acid sequence of LPXTGX (SEQ ID NO:1), wherein said peptide is labeled with a detectable marker and covalently linked to a solid support at the N-terminus of said peptide;
   (b) mixing the labeled, linked peptide with a membrane extract of gram-positive bacteria and a suspected inhibitor of said enzyme;
   (c) detecting a release of said marker from the peptide; and
   (d) comparing the release of said marker from the mixture to that released from a control mixture lacking the suspected inhibitor.

2. The method of claim 1, wherein the control mixture is reacted contemporaneously with the mixture containing the suspected inhibitor.

3. The method of claim 1, wherein said peptide comprises the sequence LPSTGE (SEQ ID NO:14).

4. The method of claim 1, wherein said bacteria is Streptococcus.

5. The method of claim 4, wherein said Streptococcus is a group A Streptococcus.

6. The method of claim 1, wherein said marker is radioactive.

7. The method of claim 1, wherein said solid support is chromatographic beads with a diameter of from about 10 to about 100 μm.

8. The method of claim 7, wherein said chromatographic beads are from about 50 to about 80 μm in diameter.

9. The method of claim 1, wherein said membrane extract is made with carbonate buffer.

10. The method of claim 9, wherein said carbonate buffer is from 0.05–2.0 M sodium carbonate.

11. The method of claim 10, wherein the carbonate buffer is 0.1 M sodium carbonate.

12. The method of claim 9, wherein said carbonate buffer is at a pH of 9–14.

13. The method of claim 12, wherein said carbonate buffer is at a pH of approximately 11.5.

14. A method for screening suspected inhibitors of an enzyme that cleaves surface proteins of gram-positive bacteria at the LPXTGX motif, comprising the steps of:

(a) providing a peptide comprising an amino acid sequence of LPXTGX (SEQ ID NO:1), wherein said peptide is labeled with a detectable marker and covalently linked to a solid support at the N-terminus of said peptide;

(b) mixing the linked peptide with said enzyme and the suspected inhibitor of said enzyme;

(c) detecting a release of said marker from the peptide; and (d) comparing the release of said marker from the mixture in step (b) to that released from a control mixture lacking the suspected inhibitor.

15. The method of claim 14, wherein the control mixture is run contemporaneous with the mixture containing the suspected inhibitor.

16. The method of claim 14, wherein said peptide comprises the sequence LPSTGE (SEQ ID NO:14).

17. The method of claim 14, wherein said bacteria is Streptococcus.

18. The method of claim 17, wherein the Streptococcus is a group A Streptococcus.

19. The method of claim 14, wherein said marker is radioactive.

20. The method of claim 14, wherein said solid support is chromatographic beads with a diameter of from about 10 to about 100 μm.

21. The method of claim 20, wherein said chromatographic beads are from about 50 to about 80 μm in diameter.

* * * * *

```
                        SEQUENCE LISTING

<160> NUMBER OF SEQ ID NOS: 18

<210> SEQ ID NO 1
<211> LENGTH: 6
<212> TYPE: PRT
<213> ORGANISM: Escherichia coli
<220> FEATURE:
<221> NAME/KEY: VARIANT
<222> LOCATION: Third and sixth amino acids in sequence
<223> OTHER INFORMATION: Variation among species of gram-positive
      bacteria

<400> SEQUENCE: 1

Leu Pro Xaa Thr Gly Xaa
       1               5

<210> SEQ ID NO 2
<211> LENGTH: 6
<212> TYPE: PRT
<213> ORGANISM: A. naeslundii or A. viscosis

<400> SEQUENCE: 2

Leu Pro Leu Thr Gly Ala
       1               5

<210> SEQ ID NO 3
<211> LENGTH: 6
<212> TYPE: PRT
<213> ORGANISM: Enterococcus faecalis

<400> SEQUENCE: 3

Leu Pro Gln Thr Gly Glu
       1               5

<210> SEQ ID NO 4
<211> LENGTH: 6
<212> TYPE: PRT
<213> ORGANISM: E. faecalis or S. cremoris

<400> SEQUENCE: 4

Leu Pro Lys Thr Gly Glu
       1               5

<210> SEQ ID NO 5
<211> LENGTH: 6
<212> TYPE: PRT
<213> ORGANISM: Enterococcus faecalis

<400> SEQUENCE: 5

Leu Pro Gln Thr Gly Glu
       1               5
```

```
<210> SEQ ID NO 6
<211> LENGTH: 6
<212> TYPE: PRT
<213> ORGANISM: group G streptococcus

<400> SEQUENCE: 6

Leu Pro Thr Thr Gly Glu
       1               5

<210> SEQ ID NO 7
<211> LENGTH: 6
<212> TYPE: PRT
<213> ORGANISM: Listeria monocytogenes

<400> SEQUENCE: 7

Leu Pro Thr Thr Gly Asp
       1               5

<210> SEQ ID NO 8
<211> LENGTH: 6
<212> TYPE: PRT
<213> ORGANISM: P. magnus

<400> SEQUENCE: 8

Leu Pro Lys Ala Gly Ser
       1               5

<210> SEQ ID NO 9
<211> LENGTH: 6
<212> TYPE: PRT
<213> ORGANISM: Staphylococcus aureus

<400> SEQUENCE: 9

Leu Pro Glu Thr Gly Glu
       1               5

<210> SEQ ID NO 10
<211> LENGTH: 6
<212> TYPE: PRT
<213> ORGANISM: Staphylococcus aureus

<400> SEQUENCE: 10

Leu Pro Glu Thr Gly Gly
       1               5

<210> SEQ ID NO 11
<211> LENGTH: 6
<212> TYPE: PRT
<213> ORGANISM: Staphylococcus aureus

<400> SEQUENCE: 11

Leu Pro Lys Thr Gly Met
       1               5

<210> SEQ ID NO 12
<211> LENGTH: 6
<212> TYPE: PRT
<213> ORGANISM: S. agalactiae

<400> SEQUENCE: 12

Leu Pro Tyr Thr Gly Val
       1               5

<210> SEQ ID NO 13
<211> LENGTH: 6
<212> TYPE: PRT
```

```
<213> ORGANISM: Staphylococcus mutans

<400> SEQUENCE: 13

Leu Pro Asn Thr Gly Glu
       1               5

<210> SEQ ID NO 14
<211> LENGTH: 6
<212> TYPE: PRT
<213> ORGANISM: S. mutans or S. pyogenes

<400> SEQUENCE: 14

Leu Pro Ser Thr Gly Glu
       1               5

<210> SEQ ID NO 15
<211> LENGTH: 6
<212> TYPE: PRT
<213> ORGANISM: S. pyogenes

<400> SEQUENCE: 15

Leu Pro Thr Thr Asn Asp
       1               5

<210> SEQ ID NO 16
<211> LENGTH: 6
<212> TYPE: PRT
<213> ORGANISM: S. pyogenes

<400> SEQUENCE: 16

Leu Pro Ser Thr Gly Ser
       1               5

<210> SEQ ID NO 17
<211> LENGTH: 6
<212> TYPE: PRT
<213> ORGANISM: S. sobrinus

<400> SEQUENCE: 17

Leu Pro Ala Thr Gly Asp
       1               5

<210> SEQ ID NO 18
<211> LENGTH: 15
<212> TYPE: PRT
<213> ORGANISM: Staphylococcus mutans

<400> SEQUENCE: 18

Lys Arg Gln Leu Pro Ser Thr Gly Glu Thr Ala Asn Pro Phe Tyr
           1               5                  10                  15
```